(12) United States Patent
Miller et al.

(10) Patent No.: US 11,617,849 B2
(45) Date of Patent: Apr. 4, 2023

(54) SENSING AND CONTROL ARRANGEMENTS FOR RESPIRATORY DEVICE

(71) Applicant: Fisher & Paykel Healthcare Limited, Auckland (NZ)

(72) Inventors: Jeremy Livingston Miller, Auckland (NZ); Nordyn Alami, Auckland (NZ); David Charles Rhodes, Auckland (NZ)

(73) Assignee: FISHER & PAYKEL HEALTHCARE LIMITED, Auckland (NZ)

( * ) Notice: Subject to any disclaimer, the term of this patent is extended or adjusted under 35 U.S.C. 154(b) by 459 days.

(21) Appl. No.: 16/525,423

(22) Filed: Jul. 29, 2019

(65) Prior Publication Data

US 2020/0023156 A1    Jan. 23, 2020

Related U.S. Application Data

(63) Continuation of application No. 14/515,438, filed on Oct. 15, 2014, now Pat. No. 10,449,320.
(Continued)

(51) Int. Cl.
*A61M 16/10* (2006.01)
*A61M 16/00* (2006.01)
(Continued)

(52) U.S. Cl.
CPC ...... *A61M 16/109* (2014.02); *A61M 16/0051* (2013.01); *A61M 16/06* (2013.01); *A61M 16/0816* (2013.01); *A61M 16/1095* (2014.02); *A61M 16/16* (2013.01); *A61M 16/161* (2014.02); *A61M 16/0069* (2014.02); *A61M 16/0875* (2013.01); *A61M 2016/003* (2013.01);
(Continued)

(58) Field of Classification Search
CPC .......... A61M 16/0003; A61M 16/0051; A61M 16/0069; A61M 16/0841; A61M 16/085; A61M 16/0875; A61M 16/1075; A61M 16/109; A61M 16/1095; A61M 16/16; A61M 2016/003; A61M 2016/0018; A61M 2016/0021; A61M 2016/0027; A61M 2016/0033; A61M 2016/0036; A61M 2016/0039; A61M 2016/102; A61M 2205/14; A61M 2205/18; A61M 2205/3306; A61M 2205/332; A61M 2205/3344; A61M 2205/3368; A61M 2205/3375; A61M 2230/005; A61M 2230/435; G01L 19/003

See application file for complete search history.

(56) References Cited

U.S. PATENT DOCUMENTS

| 4,679,573 | A | * | 7/1987 | Parnoff | ............... A61M 16/085 600/529 |
|---|---|---|---|---|---|
| 5,676,132 | A | * | 10/1997 | Tillotson | .............. A61B 5/0878 128/204.23 |
| 5,789,660 | A | | 8/1998 | Kofoed et al. | |
| 6,039,696 | A | * | 3/2000 | Bell | ...................... A61M 16/08 128/204.21 |

(Continued)

*Primary Examiner* — Joseph D. Boecker
(74) *Attorney, Agent, or Firm* — Knobbe, Martens, Olson & Bear, LLP (57) ABSTRACT

Various characteristics of a gas flow can be sensed at the end of a respiratory conduit near the patient interface using a sensing module. The sensing module can be removable from the patient end of the respiratory conduit for ease of use and ease of cleaning. The sensor module can transmit sensor data over the same wires used to heat the respiratory conduit.

14 Claims, 11 Drawing Sheets

Related U.S. Application Data (60) Provisional application No. 61/891,279, filed on Oct. 15, 2013.

(51) Int. Cl.
  *A61M 16/06* (2006.01)
  *A61M 16/16* (2006.01)
  *A61M 16/08* (2006.01)

(52) U.S. Cl.
  CPC . *A61M 2016/0027* (2013.01); *A61M 2205/14* (2013.01); *A61M 2205/18* (2013.01); *A61M 2205/332* (2013.01); *A61M 2205/3306* (2013.01); *A61M 2205/3334* (2013.01); *A61M 2205/3368* (2013.01); *A61M 2205/3375* (2013.01); *A61M 2205/42* (2013.01); *A61M 2210/0618* (2013.01); *A61M 2230/432* (2013.01); *A61M 2230/435* (2013.01); *A61M 2230/62* (2013.01)

(56) References Cited

U.S. PATENT DOCUMENTS

| | | | |
|---|---|---|---|
| 10,449,320 B2 * | 10/2019 | Miller | A61M 16/161 |
| 2004/0182392 A1 | 9/2004 | Gerder et al. | |
| 2004/0187871 A1 * | 9/2004 | Kimmel | A61B 5/4833 |
| | | | 128/204.23 |
| 2006/0118113 A1 | 6/2006 | Bremner et al. | |
| 2006/0145078 A1 | 7/2006 | Russell | |
| 2006/0229526 A1 * | 10/2006 | Chen | A61B 5/097 |
| | | | 600/532 |
| 2007/0225612 A1 | 9/2007 | Mace et al. | |
| 2011/0023874 A1 | 2/2011 | Bath et al. | |
| 2011/0108031 A1 | 5/2011 | Korneff et al. | |
| 2012/0125333 A1 * | 5/2012 | Bedford | A61M 16/06 |
| | | | 128/203.25 |
| 2012/0318266 A1 * | 12/2012 | Chou | A61M 16/024 |
| | | | 128/204.23 |
| 2014/0052014 A1 | 2/2014 | Jaffe | |
| 2014/0216459 A1 | 8/2014 | Vos et al. | |
| 2015/0101600 A1 | 4/2015 | Miller et al. | |
| 2016/0202200 A1 | 7/2016 | Nakano et al. | |

* cited by examiner

SENSING AND CONTROL ARRANGEMENTS FOR RESPIRATORY DEVICE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Technical Field

The present disclosure generally relates to sensor modules and control systems for use with gas therapy devices.

Description of the Related Art

In patients suffering from obstructive sleep apnea (OSA), muscles that normally keep the upper airway open relax during slumber to the extent that the airway is constrained or completely closed off, a phenomenon often manifesting itself in the form of snoring. When this occurs for a period of time, the patient's brain typically recognizes the threat of hypoxia and partially wakes the patient in order to open the airway so that normal breathing may resume. The patient may be unaware of these waking episodes, which may occur as many as several hundred times per session of sleep. This partial awakening may significantly reduce the quality of the patient's sleep, over time potentially leading to a variety of symptoms, including excessive daytime sleepiness, chronic fatigue, elevated heart rate, elevated blood pressure, weight gain, headaches, irritability, depression and anxiety.

Obstructive sleep apnea is commonly treated with the application of positive airway pressure (PAP) therapy. PAP therapy involves delivering a flow of gas to a patient at a therapeutic pressure above atmospheric pressure that will reduce the frequency and/or duration of apneas, hypopneas, and/or flow limitations. The therapy is often implemented by using a PAP device to deliver a pressurized stream of gases through a conduit to a patient through a patient interface or mask positioned on the face of the patient. A humidifier can be positioned in-line between the PAP device and the patient interface to heat and humidify the gases.

SUMMARY

Sensors can be used to determine characteristics of gases used in a respiratory therapy system. The determined gas characteristics can be used in the control of various components of the respiratory therapy system. For example, if the gases temperature desired at the end of a gas conduit is 37° C., if the temperature of the gases at or near the end of the conduit can be measured, then the heat output of a conduit heater can be adjusted according to a function of the desired gases temperature and the measured gases temperature to help ensure that the desired gases temperature is achieved. It is desirable to measure gas characteristics of gases as close to a patient using the respiratory therapy system as possible to improve the accuracy of models adapted to control the respiratory therapy system components or to facilitate the use of closed-loop control systems. Transmitting signals from sensors positioned relatively close to the patient to a signal receiver located, for example, at a flow generator upstream of the sensors can require the use of additional wires for data transmission, which can decrease the convenience or increase the cost of using the sensors. If usage of the sensors is not desired, their presence can unnecessarily increase the cost of the respiratory therapy system. Solutions are sought for one or more of the above concerns.

Certain features, aspects and advantages of at least one of the configurations disclosed herein include the realization that a sensor module may be positioned between components of a respiratory therapy system. For example, the sensor module can be positioned between a gases conduit and a patient interface. The sensor module can comprise a gases inlet, a gases outlet, and a lumen extending between the gases inlet and the gases outlet. The sensor module can also comprise one or more sensors adapted to measure or determine one or more characteristics of gases passing through the lumen. Data signals obtained from the sensors can be transmitted over, for example, wires used to heat the gases conduit and/or energize the sensor module by superimposing the data signals over power signals transmitted over the wires. The sensor module can releasably engage with the components of the respiratory therapy system, allowing for a modular or convenient design. Additionally, because the sensor module is not permanently joined to the gases conduit, the sensor module can be reused.

DESCRIPTION OF THE DRAWINGS

Specific embodiments and modifications thereof will become apparent to those skilled in the art from the detailed description herein having reference to the figures that follow, of which.

DETAILED DESCRIPTION

Figure 1:
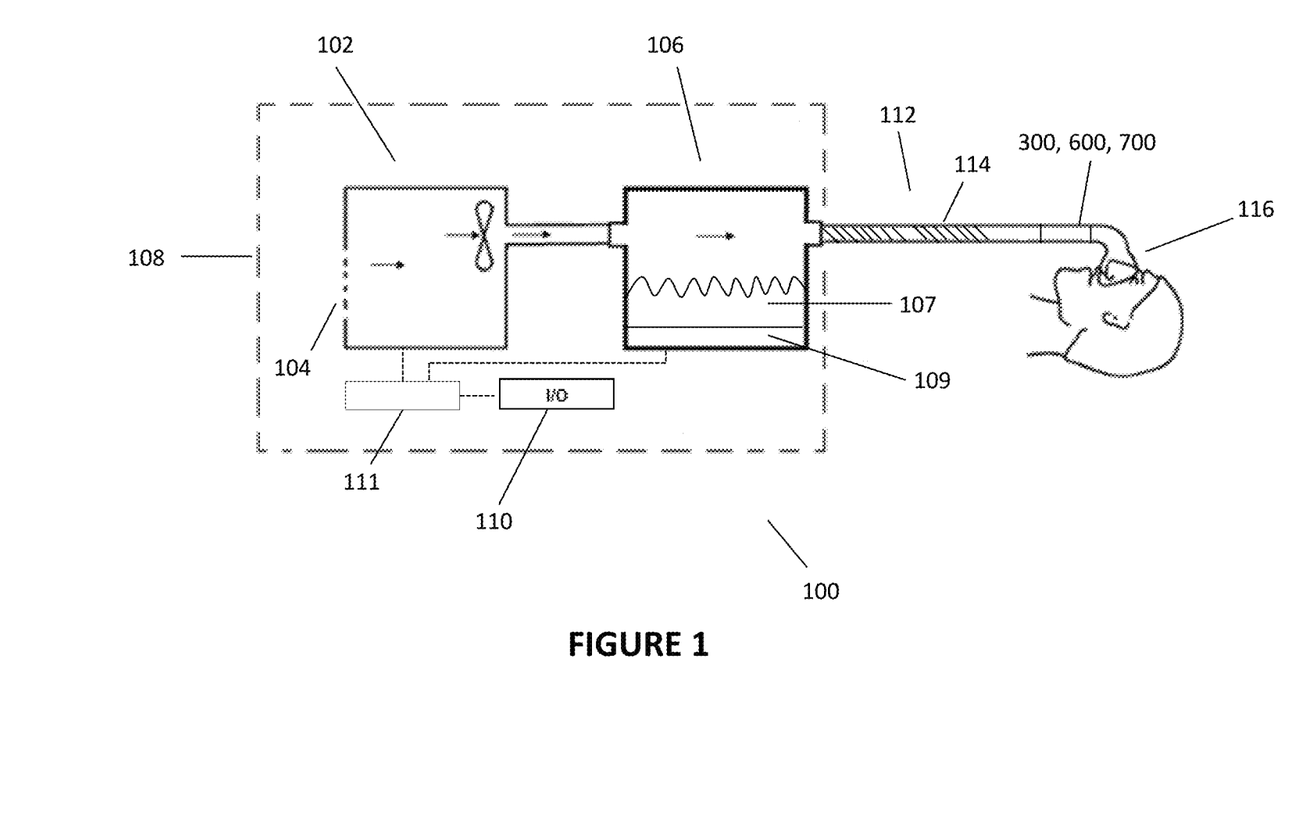
FIG. 1 shows a schematic diagram of a respiratory therapy system.

With reference to the non-limiting exemplary embodiment illustrated in FIG. 1, a respiratory therapy system 100 is shown. The respiratory therapy system 100 comprises a flow generator 102. The flow generator 102 comprises a positive airway pressure or PAP device. The flow generator 102 receives gases from a gases inlet 104 and propels them to a humidifier 106. The flow generator 102 and humidifier 106 may be part of an integrated flow delivery system or may share a housing 108. The humidifier 106 heats and humidifies the gases. The humidifier 106 comprises a quantity of water or another moisturizing agent 107 (hereinafter referred to as water). The humidifier 106 also comprises a heating plate 109 that may be used to heat the water in the humidifier 106 to encourage water vaporization and/or entrainment in the gas flow and increase the temperature of gases passing through the humidifier 106. The heating plate may, for example, comprise a resistive metallic heating plate. Heated and humidified gases are passed from a humidifier outlet to a gases conduit 112. The gases conduit 112 comprises a heating wire 114. The heating wire 114 reduces or prevents the condensation of moisture along the walls of the gases conduit 112. The heating wire 114 is positioned in, on, around or near the gases conduit 112. Gases are passed from the gases conduit 112 to a patient interface 116 through which they are delivered to a patient. The respiratory therapy system 100 comprises a controller 111 that controls the operation of the flow generator 102. The controller 111 also controls the operation of the humidifier 106. The respiratory therapy system 100 comprises an input/output (I/O) module 110. The I/O module 110 comprises a way for a user to interact with and set parameters for the flow generator 102 and/or humidifier 106 (including but not limited to target gases humidity levels, target gases temperature levels and target gases pressure levels) as well as receive information regarding the operation of the respiratory therapy system 100 and/or its components. The I/O module 110 may comprise, for example, buttons, knobs, dials, switches, levers, touch screens, speakers, displays and/or other input or output elements. In some configurations, the humidifier 106 may not be present. In some configurations, the flow generator 102 may comprise elements other than PAP devices, including but not limited to high flow therapy devices or ventilation devices. In some configurations, the patient interface 116 may comprise a sealing, semi-sealing or non-sealing interface. For example, the patient interface 116 may comprise an oral mask, an oro-nasal mask, a full face mask, a nasal pillows mask, an endotracheal tube, a combination of the above, or some other gas conveying system or apparatus.

As seen in FIG. 1, the respiratory therapy system 100 includes a sensor module 300, 600, 700. The sensor module 300, 600, 700 is configured to be removably attached to the gases conduit 112 and to the patient interface 116. The sensor module 300, 600, 700 comprises one or more sensors adapted to determine one or more characteristics of gases passing through or along the sensor module 300, 600, 700. The sensors can include, for example, one or more of a relative humidity sensor, an absolute humidity sensor, a temperature sensor, a dew point sensor, an enthalpy sensor, a pressure sensor, a flow rate sensor, an oxygen sensor, a $CO_2$ sensor, or a nitrogen sensor, but can include one or more other sensors. In some configurations, the sensor module 300, 600, 700 can comprise one or more sensors adapted to determine one or more characteristics of a patient using the respiratory therapy system 100 or of the ambient environment outside of the respiratory therapy system 100. The sensors can include, for example, one or more of an acoustic sensor or microphone, a light sensor or camera, an ambient temperature sensor, an ambient humidity sensor, or an accelerometer, but can include one or more other sensors. In other configurations, the sensor module 300, 600, 700 can be positioned between, at or near other components of the respiratory therapy system 100. For example, the sensor module 300, 600, 700 can be positioned between the flow generator 102 and the humidifier 106, or between the humidifier 106 and the conduit 112. The sensor module 300, 600, 700 is further described in the following disclosure with reference to the accompanying figures.

Some possible utilities for some such sensors present in the sensor module 300, 600, 700 are disclosed below.

Pressure and/or flow sensors may be used within the sensor module 300, 600, 700 to obtain a measure of flow data, flow waveforms, pressure data and/or pressure waveforms proximal to the patient. The data or waveforms can be used, for example, to feed information into algorithms adapted to facilitate apnea or hypopnea detection, pressure/flow control, expiratory pressure relief, and/or automatic pressure control/titration algorithms.

Enthalpy sensors may be used within the sensor module 300, 600, 700 to obtain a measure of the heat energy of gases present proximal to the patient. Measured enthalpy values may be used to calculate the level of heat energy and/or humidity delivered to the patient.

Light sensors may be used to monitor the light level of the environment around the sensor module 300, 600, 700. For example, if the light level of the environment is lower than a threshold light level, the patient may have turned off the lights in a room in preparation to sleep. The sensor module 300, 600, 700 may then send a signal to the controller 111 to initiate therapy.

Acoustic sensors/microphones may be used to monitor the level of noise in the respiratory therapy system 100 and/or in the environment outside of the respiratory therapy system 100. They may be used to, for example, detect patient snoring or other noises that indicate the presence of an apnea or hypopnea event. The sensor module 300, 600, 700 may transmit some such sensor signals to the controller 111, which may in turn use such data to control, for example, the flow generator 102 to modulate the level of pressure of gases delivered. If the sound level of the environment is less than a threshold, the patient may be preparing to sleep, and so a signal may be communicated to the controller 111 to initiate therapy. In some configurations, an acoustic sensor may be used to aid in the diagnosis of fault conditions of, for example, a motor of the flow generator 102.

$CO_2$ and $O_2$ sensors, if supplemental oxygen and/or carbon dioxide are being delivered using the respiratory therapy system 100, may be used to help determine the efficacy of the oxygen or carbon dioxide delivery therapy. In some configurations, the sensors may be used to determine the efficacy of, for example, a bias flow or venting mechanism used in or on the patient interface 116 or elsewhere in the respiratory therapy system 100.

Accelerometer/gyroscopic sensors may be used to determine the orientation of the user during slumber, particularly when the sensor module 300, 600, 700 is secured to the patient interface 116. Information regarding the orientation may be used to modulate the pressure of delivered gases (through, for example, adjustment of the operation parameters of the flow generator 102) to treat the patient and/or improve the comfort of therapy. For example, if the patient is in a prone position, the risk of hypopnea and/or apnea events may be less than if the patient is supine. In some configurations, then, the pressure of gases delivered may be decreased if the accelerometer determines that the patient is positioned in the prone position.

Figure 2A:
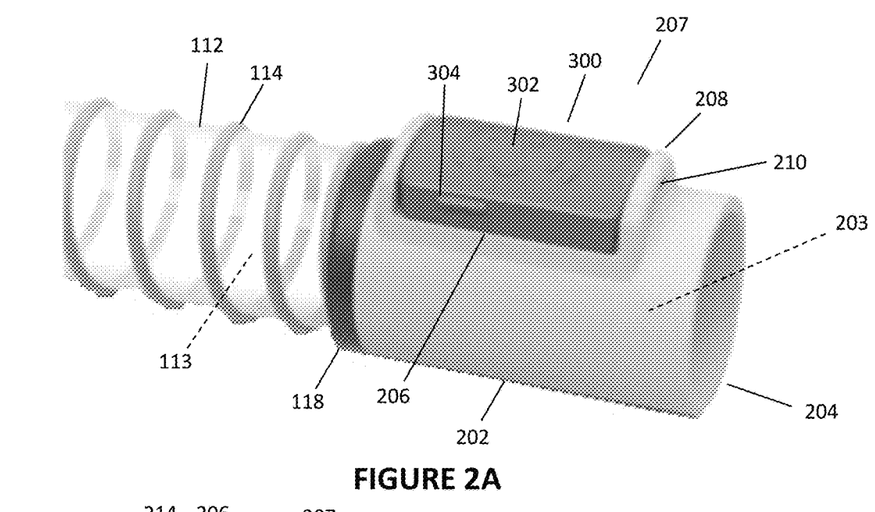
FIGS. 2A-2C show various perspective views of a sensing system and components thereof.
Figure 2B:
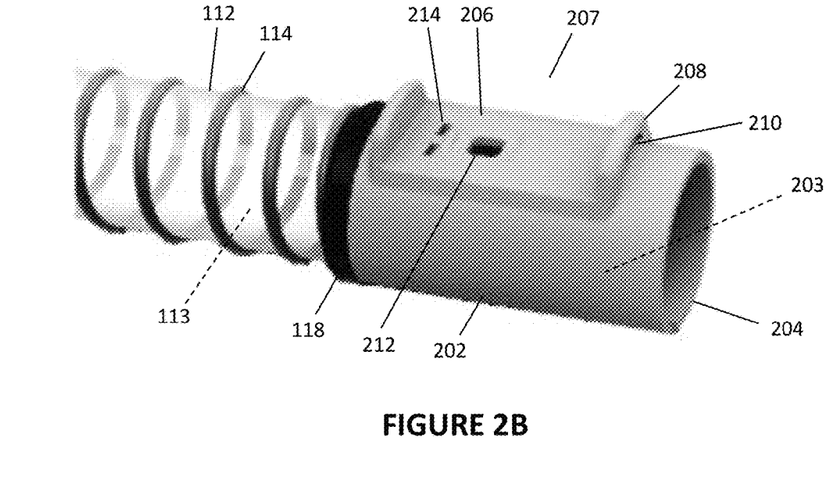
Figure 2C:
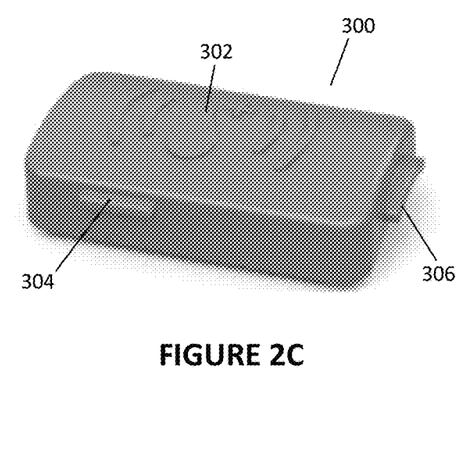

FIGS. 2A-2C show a non-limiting first exemplary configuration for a sensing system incorporating a sensor module 300. As shown, the gases conduit 112 (comprising heater wire 114 and gases passageway or lumen 113) comprises a cuff 118. The cuff 118 is overmoulded with an overmould structure 202. The overmould structure 202 may comprise, for example, an overmoulded layer of silicone. The overmould structure 202 comprises a lumen 203 in pneumatic communication with the lumen 113 and an outlet 204. The outlet 204 may pneumatically interface with, for example, the patient interface 116 described elsewhere in this disclosure with reference to FIG. 1. The overmould structure 202 additionally comprises a region 207 adapted to accommodate the sensor module 300. The region 207 comprises a ridged and raised section 208. The ridged and raised section 208 comprises an aperture 210. The ridged and raised section 208 defines a recessed area 206 in which the sensor module 300 is held. The sensor module 300 comprises a side protrusion 306 adapted to fit through the aperture 210 (through, for example, a snap fit mechanism) to help retain the sensor module 300 in the recessed area 206. The side protrusion 306 can be beveled or substantially arcuate in such a way that promotes both easy retainment and release of the sensor module 300 from the recessed area 206 and aperture 210. The sensor module 300 can also comprise a tab 304. The tab 304 can be pressed by a patient or user to facilitate the extraction of the sensor module 300 from the recessed area 206. The sensor module 300 comprises an insignia or symbol 302 that can inform the patient or user as to the capabilities of the sensor module. For example, a teardrop symbol 302 as shown in FIGS. 2A and 2C might imply that the sensor module 300 is capable of humidity sensing. In other configurations, the sensor module 300 might have no insignia or symbol 300. In other configurations, the sensor module 300 can interface with the overmould structure 202 and/or conduit 112 via other means, including but not limited to latch/catch arrangements and adhesives.

FIG. 2B shows that the recessed area 206 comprises an electrical interface 214. The electrical interface 214 comprises a pair of electrical terminals that interface with corresponding or complementary electrical terminals on the sensor module 300. The electrical interface 214 permits electrical communication between the sensor module 300 and the heating wire 114, and in turn the heating wire 114 is electrically linked to the controller 111. Through the electrical interface 214, the sensor module 300 can transmit a data signal to a controller located upstream from the sensor module 300. For example, the data signal can be transmitted to the controller 111 adapted to control the flow generator 102 and/or humidifier 106 as described elsewhere in this disclosure with reference to FIG. 1. The data signal may be overlaid or superimposed over a power signal that passes through the heating wire 114 to provide power to the sensor module 300 and/or provide resistive heating to the heating wire 114. In other configurations, the data signal may be transmitted to components of the respiratory therapy system 100 wirelessly, e.g. using RFID or wireless communications technologies including but not limited to Wi-Fi, Bluetooth, 2G, 3G, or 4G. Further attention is given to the details of data transfer elsewhere in this disclosure with reference to the accompanying figures.

The recessed area 206 additionally comprises a gases sampling aperture 212. The gases sampling aperture 212 at least in part defines a gases sampling passageway extending between the lumen 203 and one or more sensors positioned within the sensor module 300. The gases sampling aperture 212 in use seals against the sensing module 300. In some configurations, a section of the recessed area 206 defining the gases sampling aperture 212 may be adapted to seal against the sensing module 300. In other configurations, a section of the recessed area 206 defining the gases sampling aperture 212 and/or a section of the sensor module 300 defining a complementary aperture of the sensor module 300 at least in part defining the gases sampling passageway may comprise a sealing structure configured to promote pneumatic sealing between the recessed area 206 and the sensor module 300.

Figure 3:
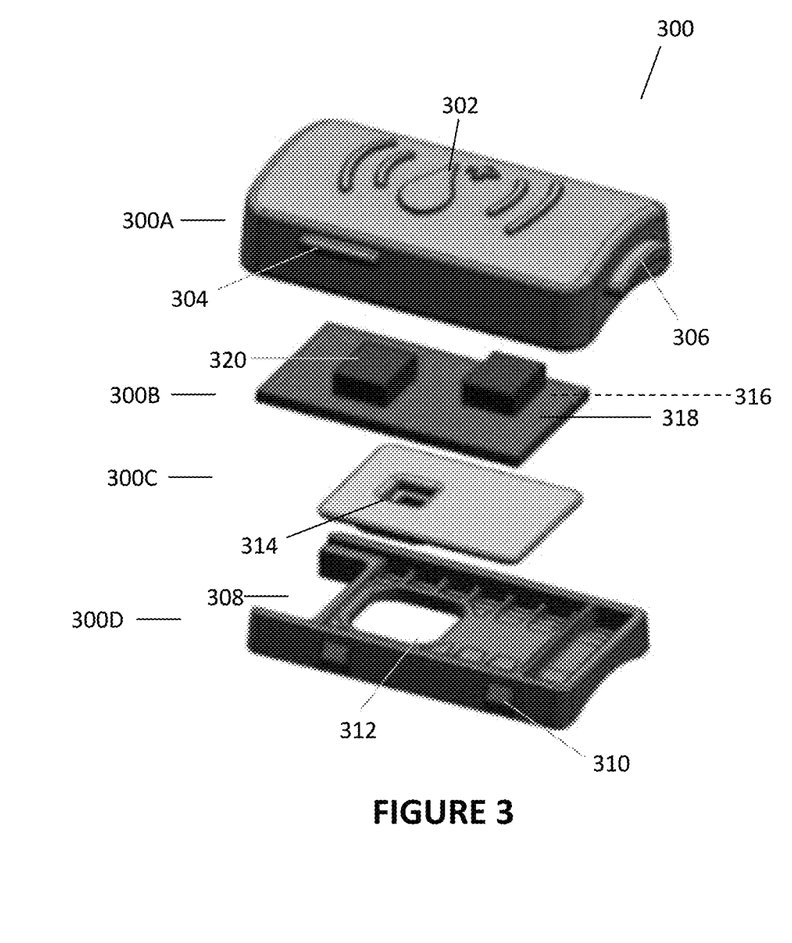
FIG. 3 shows an exploded view of a sensor module.

FIG. 3 demonstrates an exploded view of the sensor module 300 shown in FIGS. 2A and 2C. The sensor module 300 comprises a module base 300D, a module seal 300C, a printed circuit board (PCB) 300B, and a module cover 300A. The module base 300D is adapted to support the sensor module 300. The module base 300D comprises a base aperture 312 in pneumatic communication with the gases sampling aperture 212 present on the recessed area 206. Gases entering the sensor module 300 through the base aperture 312 are channeled through a seal aperture 314 of the module seal 300C. The module seal 300C can be produced from silicone or another material adapted to promote a sealed gas passageway between the sensor module 300 and the recessed area 206 of the overmould structure 202. Gases passing through the seal aperture 314 contact one or more sensors 316 positioned on the bottom of the PCB 300B. The PCB 300B comprises a microcontroller 320 adapted to receive data signals from the one or more sensors 316 and transmit the data signals over the heating wire 114 (at a heating wire termination portion contacting the PCB 300B through the recess 308 present in the module base 300A, not shown) (using, for example, a power signal modulator). The module cover 300A protects the PCB 300B and the gases sampling passageway in the sensor module 300. The module cover 300A interfaces with the module base 300D via a catch/latch mechanical fastener arrangement through the use of latches 310 present on the exterior of the module base 300D and complementary catches (not shown) present in the inside of the module cover 300A. In some configurations, the module base 300D may comprise a single latch 310 and the module cover 300A may comprise a single catch. In some configurations, the module base 300D may comprise catches and the module cover may comprise complementary latches. In some configurations, the module base 300D and the module cover 300A may be joined to one other using some other means, including but not limited to ultrasonic welding, radiofrequency welding, mechanical push-fit arrangements, adhesives, and pins. In some configurations, the PCB 300B and the module cover 300A may comprise apertures allowing pneumatic communication between the gases sampling passageway of the sensor module 300 and the ambient atmosphere outside of the sensor module 300 and/or outside of the respiratory therapy system 100. Allowing sensed gas to leak from the sensor module 300 can reduce the chance of moisture build-up on the PCB 300B and can help to cool the PCB 300B.

In some configurations, a membrane or filter may be used to protect the sensor module 300, reduce the potential for the introduction of contaminants and/or pathogens into the lumen and/or gases sampling passageway, and/or reduce the potential for delivery of contaminants and/or pathogens to the patient. The membrane or filter may be permanent or removable and/or replaceable, and may be present in the lumen 113, present in the cuff 118, or present in the gases sampling passageway. In some configurations, a membrane or filter can be attached to or surround the sensor module 300 or around one or more components of the sensor module, including but not limited to the PCB 318 or sensor(s) 316. The membrane or filter may be constructed from a material that can permit the passage of water vapour while preventing the passage of liquid water (e.g. such as but not limited to stretched or expanded polytetrafluoroethylene (PFTE) or Gore-Tex™). In some configurations, the membrane or filter may be constructed from an anti-bacterial material or comprise one or more anti-bacterial compounds or compositions, such as but not limited to silver particulates.

Figure 4:
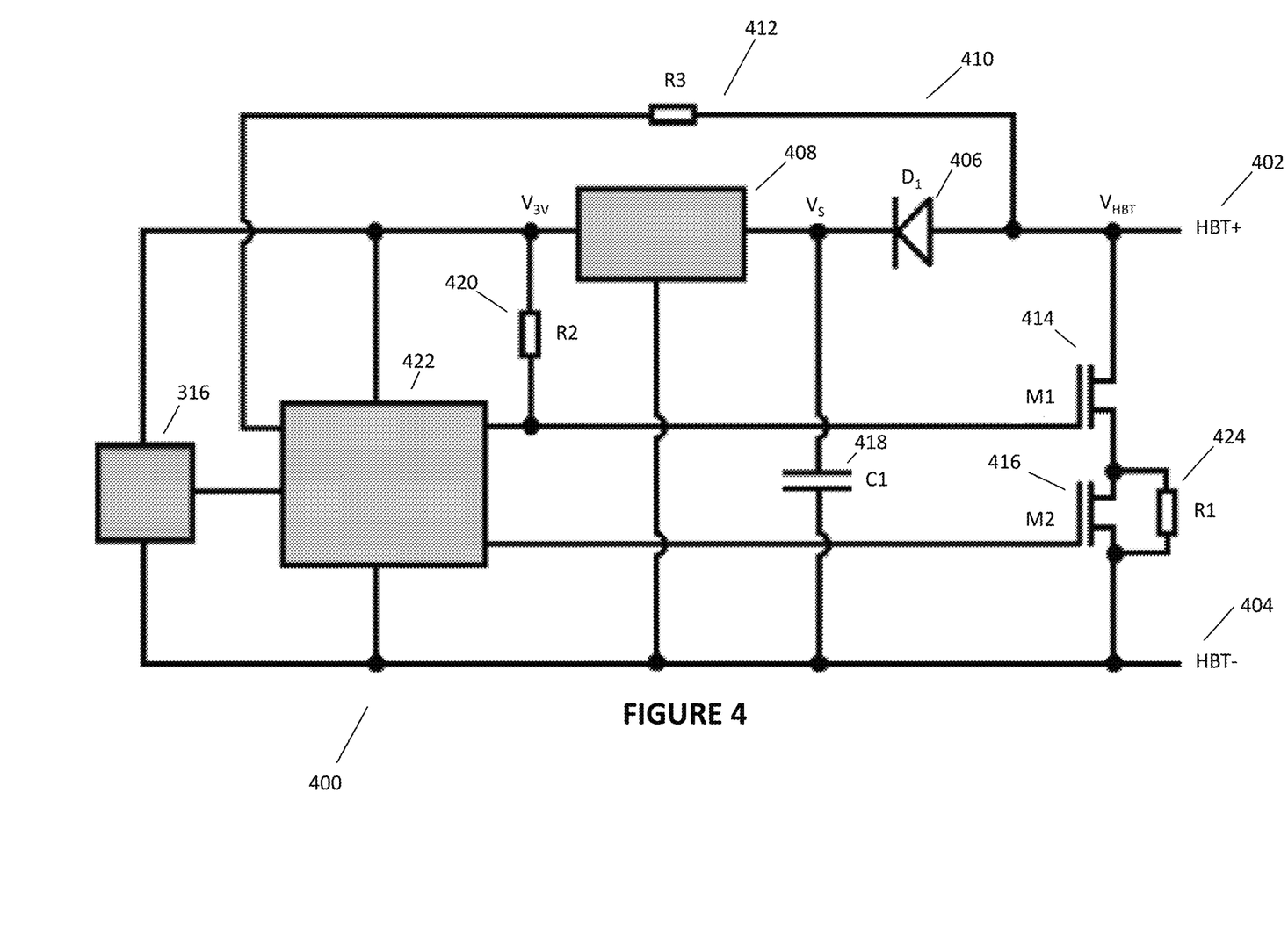
FIG. 4 shows a circuit diagram.

FIG. 4 shows a non-limiting exemplary circuit diagram 400 demonstrating a schematic for the PCB 300B. The sensor module 300 stores power in a capacitor 418 located on the PCB 300B to read and transmit data signals from the one or more sensors 316. The data signals are transmitted to, for example, the controller 111 described elsewhere in this disclosure with reference to FIG. 1, over, for example, the heating wire 114 of the conduit 112 described with reference to FIG. 1. This transmission occurs by modulating the current passing through the heating wire 114 (via a modulator in the sensor module 300) to include a data packet. The data packet is sent along the heating wire 114 to a demodulator upstream of the modulator. The modulator may comprise a metal-oxide-semiconductor field-effect transistor (MOSFET)-based data shunt 416 configured to switch on and off an added resistance to the current, optionally transmitting data encoded in a non-return-to-zero (NRZ) fashion. In some configurations, the data packets generated by the modulator allow for the generation and transmission of relatively high (1) and relatively low (0) currents, creating a sequence of bytes representing data signals. In some configurations, the data packets may be encoded in such a way that allows for data and clock signals to be combined into a single synchronized data stream, such as by the use of Biphase Mark Code (BMC, or Differential Manchester Encoding). In some configurations, a CRC error detection packet may be transmitted together with one or more of the data packets to aid the demodulator in, for example, discarding erroneous or implausible data packets containing excess noise and/or interference. In some configurations, the degree of modulation of the peak current observed in the heating wire 114 is limited to 1% or about 1% of the peak current.

Connected to the heating wire 114 is a diode 406 that feeds current to the capacitor 418 of the PCB 300B. At the beginning of a pulse-width modulation (PWM) cycle (e.g. used to control a duty cycle of the heating wire 114), the capacitor 418 begins to charge. To prevent the capacitor 418 from overcharging, a transistor (e.g. MOSFET) power shunt 414 can be placed along the heating wire circuit. When the voltage across the capacitor 418 reaches a maximum allowable level (e.g. a predetermined level), a microcontroller 422 of the PCB 300B switches on the power shunt 414, shorting the heating wire terminals 402, 404 such that the voltage across the capacitor 418 stops rising. The diode 406 prevents the charge in the capacitor 418 from flowing back into the heating wire circuit. In some configurations, the resistance of the heating wire 114 and the capacitance of the capacitor 418 are such that the rate of increase of voltage across the heating wire 114 is slow enough that the microcontroller 422 has enough time to measure the voltage across the capacitor 418 and turn on the power shunt 414 to limit excessive voltage rises across the capacitor 418.

It has been discovered that in some cases, during start-up of the PCB 300B the microcontroller 422 may take a long time to warm up and run code to measure the voltage across the capacitor 418. This time may be too long relative to the rate of increase in voltage across the heating wire circuit, and the risk of damage to the PCB 300B increases. In some configurations, then, a resistor 424 may be placed in a circuit that connects a $V_{3V}$ rail (see FIG. 4) to the power shunt 414. The resistor 424 helps to allocate voltage more evenly between the power shunt 414 and the $V_{3V}$ rail. As the power shunt 414 reaches a predetermined turn-on voltage, the power shunt 414 short-circuits the heating wire 114 to protect the PCB 300B. In some circumstances, with the above configuration, when the power shunt 414 is reactivated, the voltage across a $V_s$ rail may not be high enough, and a discharge resetting the microcontroller 422 may occur. In some such configurations, the microcontroller 422 can be programmed to turn off the power shunt 414 to allow the capacitor 418 to charge to the maximum allowable level. After the capacitor 418 is charged, the power shunt 414 may be activated as described herein.

In some configurations, the microcontroller 422 may operate according to a software loop. The loop may be triggered by an interrupt pin (shown in FIG. 4 as the wire 410 connected to the resistor $R_3$ 412) of the microcontroller 422, the interrupt pin in turn connected to the heating wire 114 positive input HBT+. As the PWM cycle initiates, the interrupt pin 410 may be triggered, which can cause the microcontroller 422 to wake from a sleep state. Once awake, the microcontroller 422 may check for the value of the voltage across the $V_s$ rail that was present at the end of the previous PWM cycle. If the voltage was less than or equal to a minimum allowable value, a charge cycle may be initiated. If the voltage was greater than a minimum allowable value, a data cycle may be initiated. In the event that a charge cycle is initiated, the data shunt 416 may be shut off to allow the voltage across the $V_s$ rail to rise. The microcontroller 422 may continually sample the value of the voltage across the $V_s$ rail. When the microcontroller 422 determines that the voltage across the $V_s$ rail reaches a maximum allowable value, the microcontroller 422 may turn on the power shunt 414 to prevent a further rise in the voltage across the $V_s$ rail. In the event that a data cycle is initiated, the power shunt 414 may be turned on to prevent further rises in the voltage across the $V_s$ rail, and the microcontroller 422 may then wait for a brief period of time to mitigate transient background signal noise sometimes detected along the heating wire 114. Data signals from the one or more sensors 316 may then be prepared to be transmitted using the data shunt 416. When the charge or data cycle is complete, the microcontroller 422 receives the data signals and transmits one or more data packets across the heating wire 114 to the controller 111 based on the data signals received. Once the data packets have been transmitted, the microcontroller 422 samples and records the voltage across rail $V_s$ for the next iteration of the loop and monitors the PWM cycle. If the PWM is low, then the microcontroller 422 enters a sleep mode to be awakened on another cycle.

Figure 5A:
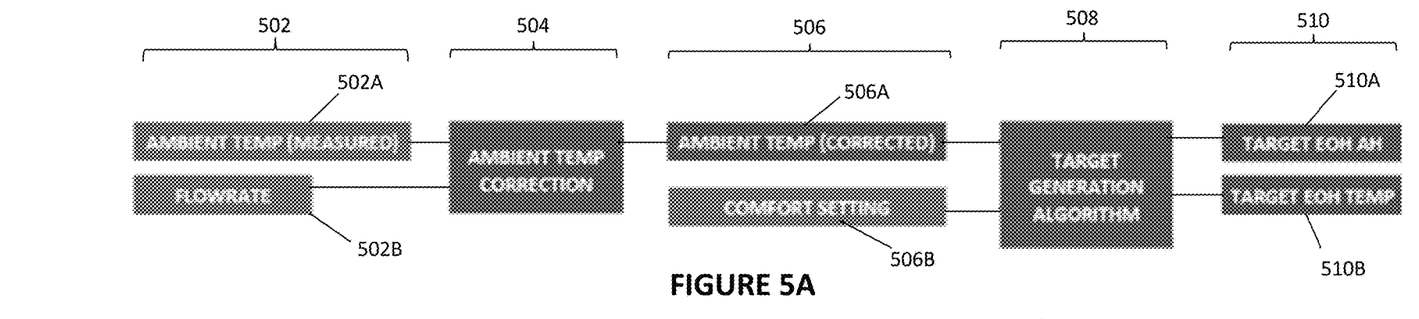
FIGS. 5A-5B show control algorithms for a respiratory therapy system.
Figure 5B:
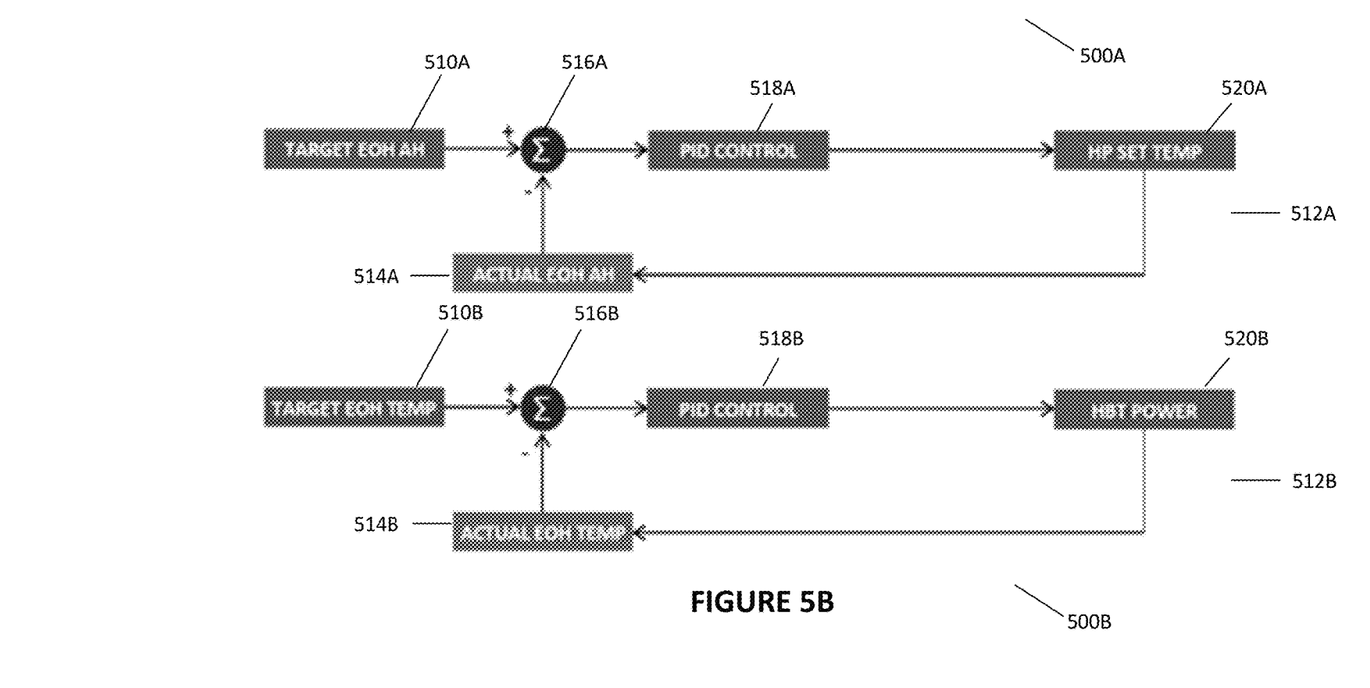

FIGS. 5A and 5B describe non-limiting exemplary control algorithms 500A and 500B that may be used together with data obtained by the sensor module 300, assuming that the sensor module is positioned between a gases conduit and a patient interface (e.g. in an 'end-of-hose' or EOH position). First control algorithm 500A deals with calculation of target EOH absolute humidity (AH) and target EOH temperature values. In 502A, the ambient temperature is measured (for example, by an ambient temperature sensor of the respiratory therapy system 100). A gases flow rate is measured (see 502B) (for example, by using a flow rate sensor positioned in the respiratory therapy system 100). In 504, a new ('corrected') ambient temperature is calculated based on a function of the old ambient temperature and the measured gases flow rate. In 506, the corrected ambient temperature (506A) together with one or more 'comfort settings' representing desired parameters (including but not limited to desired output gas temperatures and desired output gas humidity (relative or absolute)) (see 506B; obtained, for example, using the I/O module 110 described elsewhere in this disclosure with reference to FIG. 1) are fed into a target generation algorithm (508). The target generation algorithm determines a target EOH absolute humidity value (510A) and a target EOH temperature value (510B) based on the input corrected ambient temperature and the comfort settings.

The second control algorithm 500B deals with the use of the target EOH absolute humidity value 510A and the target EOH temperature value 510B to facilitate closed loop control of components of the respiratory therapy system 100. With further reference to FIG. 5B, the target EOH absolute humidity value 510A can be used in a first closed loop control algorithm 512A to control the temperature or duty cycle of the humidifier heater plate 109. The target EOH absolute humidity value 510A is compared to the actual EOH absolute humidity value 514A (determined, for example, using a sensor 316 of the sensor module 300) using a comparing module 516A. The comparing module 516A determines the percent difference between the target and actual absolute EOH humidity values 510A, 514A and feeds the difference into a closed loop control system 518A (e.g. a proportional-integral-derivative or PID control system). The closed loop control system 518A adjusts the temperature or duty cycle of the humidifier heater plate 109, which in turn affects the actual EOH absolute humidity value 514A. The first closed loop control algorithm 512A may continually iterate to adjust the actual EOH absolute humidity value 514A such that it approaches and maintains a value or range of values close to the target EOH absolute humidity value 510A.

The target EOH temperature value 510B can be used in a second closed loop control algorithm 512B to control the temperature or duty cycle of the heating wire 114. The target EOH temperature value 510B is compared to the actual EOH temperature value 514B (determined, for example, using a sensor 316 of the sensor module 300) using a comparing module 516B. The comparing module 516B determines the percent difference between the target and actual EOH temperature values 510B, 514B and feeds the difference into a closed loop control system 518B (e.g. a proportional-integral-derivative or PID control system). The closed loop control system 518B adjusts the temperature or duty cycle of the heating wire 114, which in turn affects the actual EOH temperature value 514B. The second closed loop control algorithm 512B may continually iterate to adjust the actual EOH temperature value 514B such that it approaches and maintains a value or range of values close to the target EOH temperature value 510B.

Figures 6A, 6B, 6C:
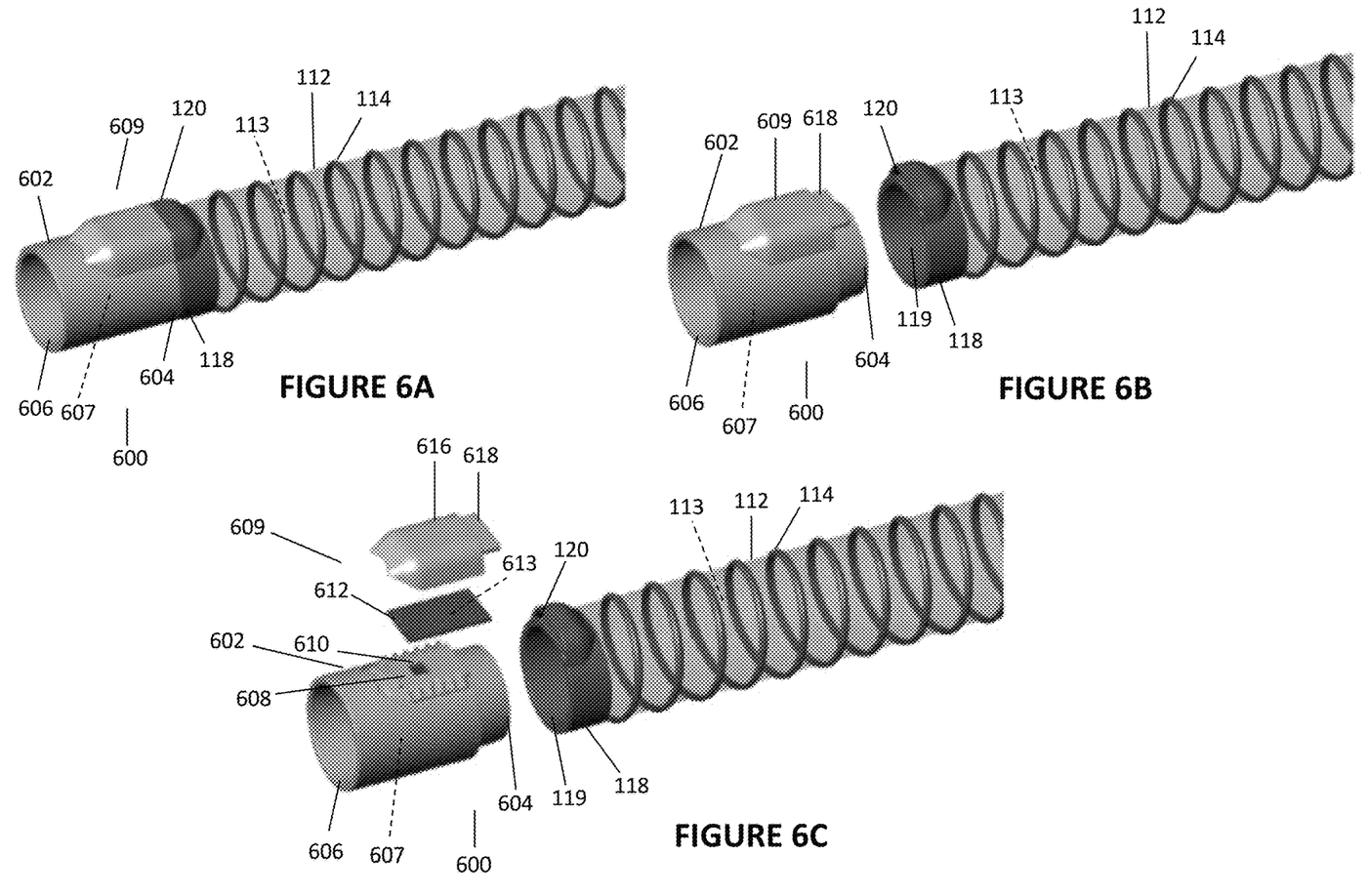
FIGS. 6A-6C show various perspective views of a sensing system and components thereof.

FIGS. 6A-6C show a non-limiting second exemplary configuration for a sensing system incorporating a sensor module 600. As shown, the gases conduit 112 (comprising heating wire 114 and gases passageway or lumen 113) comprises a cuff 118. The cuff 118 comprises an outlet 119 and a slot 120. The slot 120 comprises a pair of terminal electrical contacts (not shown) linked to a portion of the heating wire 114. The sensor module 600 can be attached to the outlet 119. The sensor module 600 comprises a body 602, an inlet 604 and an outlet 606. A lumen 607 extends between the inlet 604 and the outlet 606. The module additionally comprises a sensing element 609. As shown in FIG. 6C, the sensing element 609 rests on a recessed area 608 of the body 602. The recessed area 608 comprises an aperture 610 in pneumatic communication with the lumen 607. The sensing element 609 comprises a PCB 612 comprising one or more sensors 613 positioned on a side of the PCB 612 in pneumatic communication with the aperture 610. The gases passageway extending between the lumen 607 and the one or more sensors 613 acts as a gases sampling passageway. To protect the PCB 612, the PCB 612 is sandwiched between the recessed area 608 of the body 602 and a sensing element cover 616. The sensing element cover 616 comprises a protrusion 618 that fits into the slot 120 to allow for connection between the sensor module 600 and the cuff 118. Joining the protrusion 618 with the slot 120 additionally allows for electrical communication between the PCB 612 and the terminal portion of the heating wire 114.

Figure 7A:
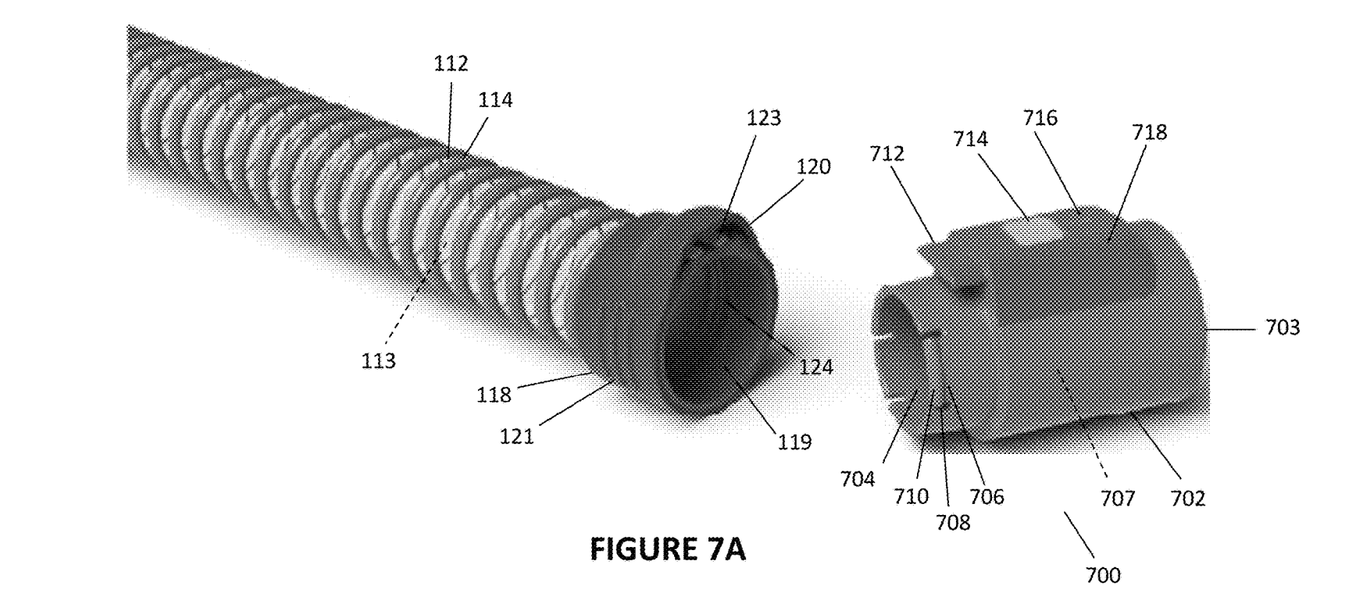
FIGS. 7A-7I show various perspective views of a sensing system and components thereof.

FIGS. 7A-7I show a non-limiting third exemplary configuration for a sensing system incorporating a sensor module 700. As shown in FIG. 7A, the gases conduit 112 (comprising heating wire 114 and gases passageway or lumen 113) comprises a cuff 118. The cuff 118 comprises an outlet 119 and a slot 120. The slot 120 comprises a pair of terminal electrical contacts 123 linked to a portion of the heating wire 114. Sections of the inner wall of the cuff 118 comprise depressions 124. The cuff 118 additionally comprises a grip section 121. The grip section 121 comprises protrusions, ridges or other surface details allowing a patient or other user to handle the cuff 118. The sensor module 700 comprises a body 702, an inlet 704 and an outlet 703. A lumen 707 extends between the inlet 704 and the outlet 703. End portions 706 of the body 702 comprise recesses 708. The recesses 708 allow the end portions 706 to cantilever in a plane substantially transverse to the lumen 707. The end portions 706 additionally comprise curved ridges 710. The sensor module additionally comprises a sensing element 718. The sensing element 718 comprises a protrusion 712 that interfaces with the slot 120, allowing for electrical communication between the terminal electrical contact 123 and an exposed PCB contact 724 of a PCB 725 positioned within the sensing element 718 (see FIG. 7I). The PCB 725 comprises sensors that may receive gases via a gases sampling passageway defined by a second aperture 720 in communication with a first aperture 717 present within the lumen 707 (see FIG. 7H). A seal 722 may be present between the first and second apertures 717, 720 to maintain a sealed gases sampling passageway.

Figure 7B:
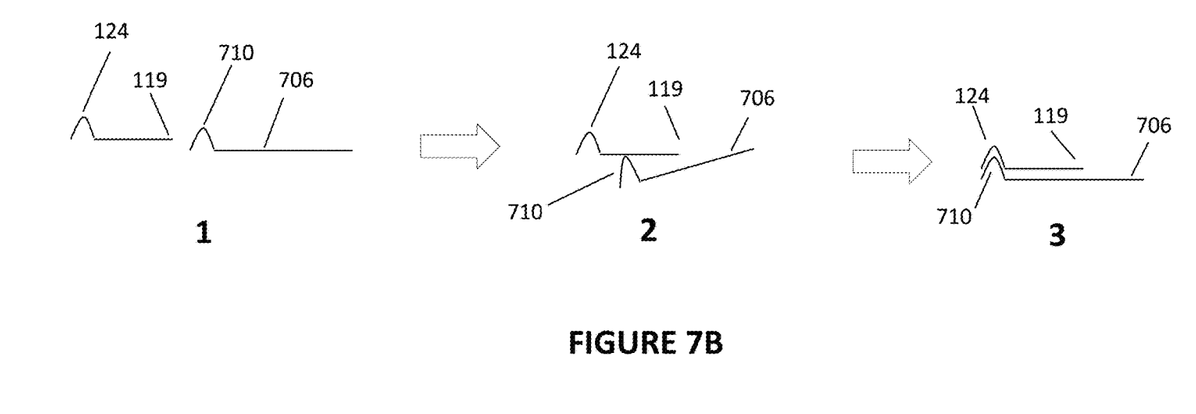
Figure 7C:
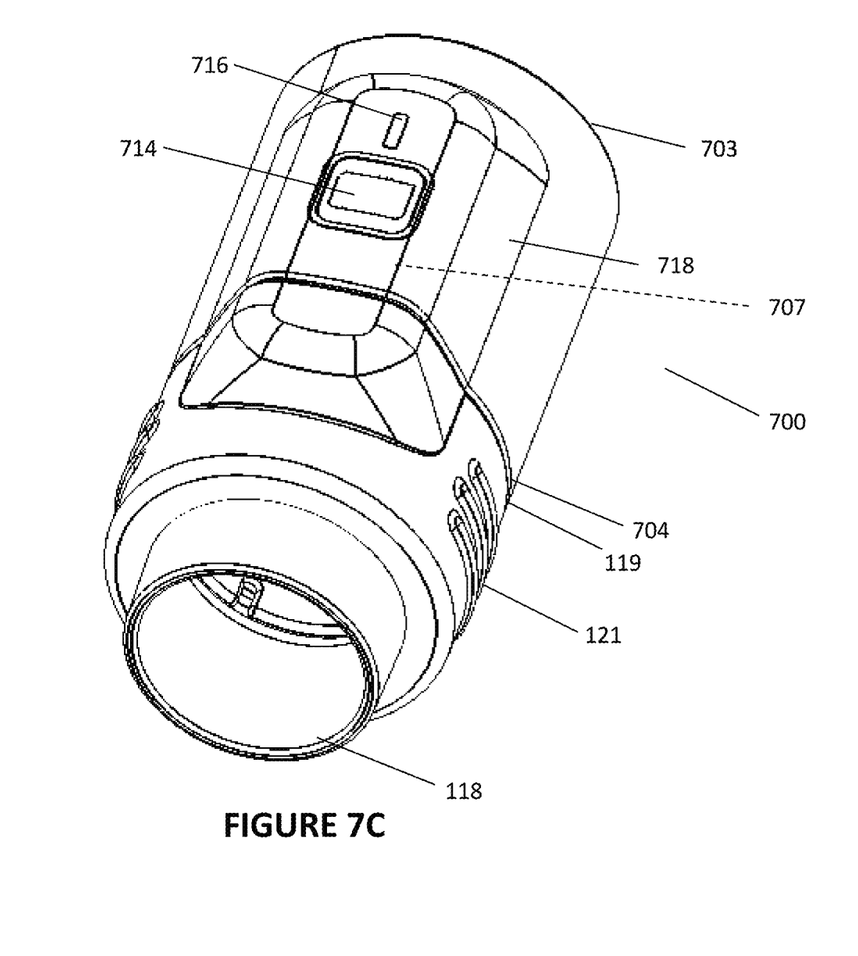
Figure 7D:
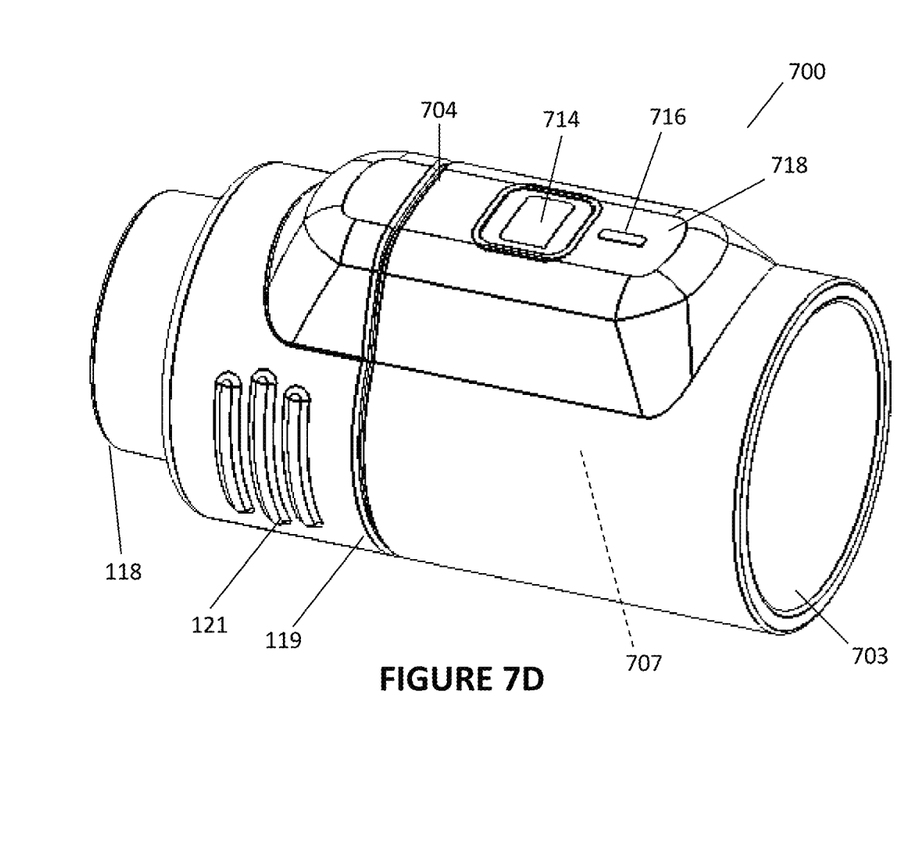
Figure 7E:
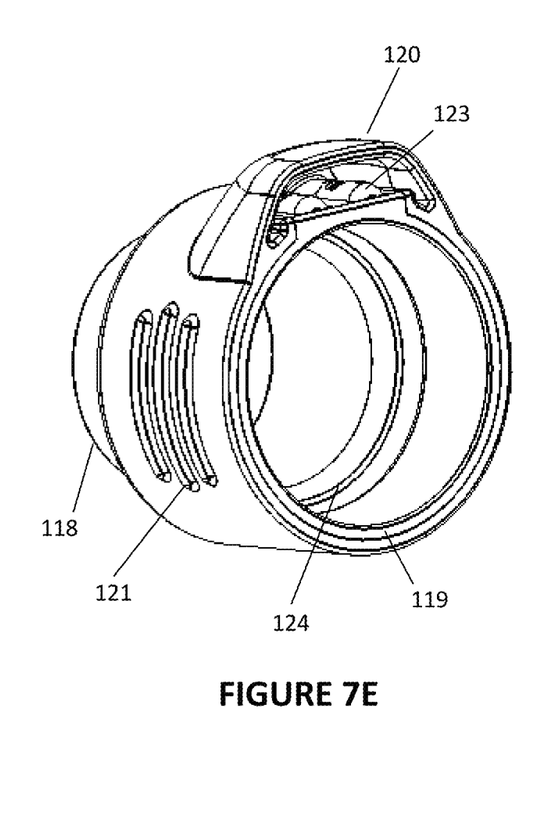
Figure 7F:
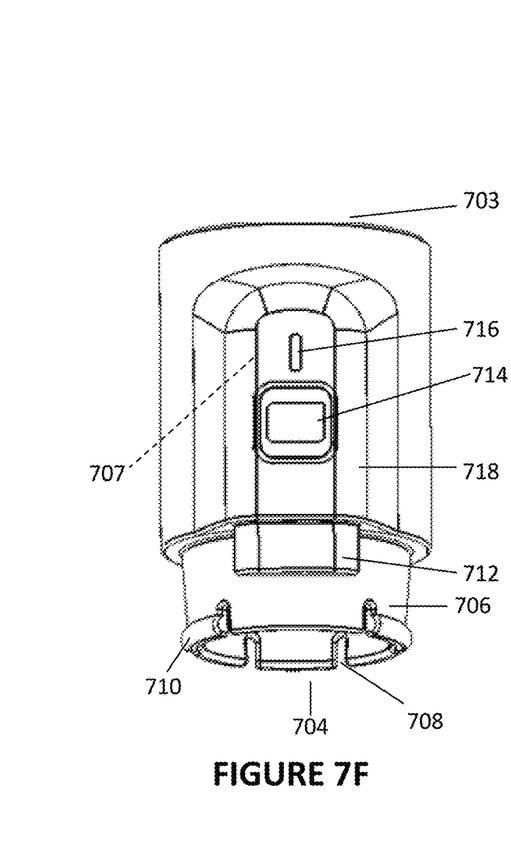
Figure 7G:
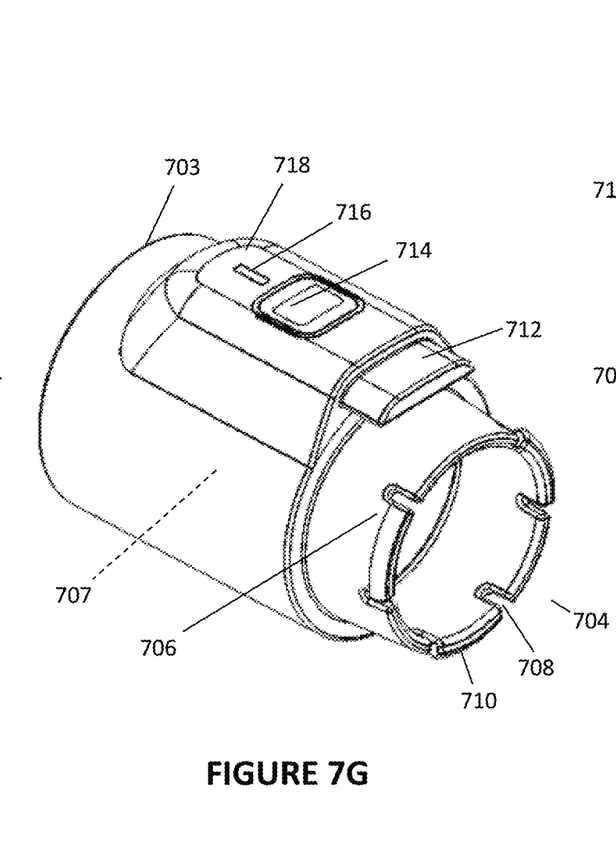
Figure 7H:
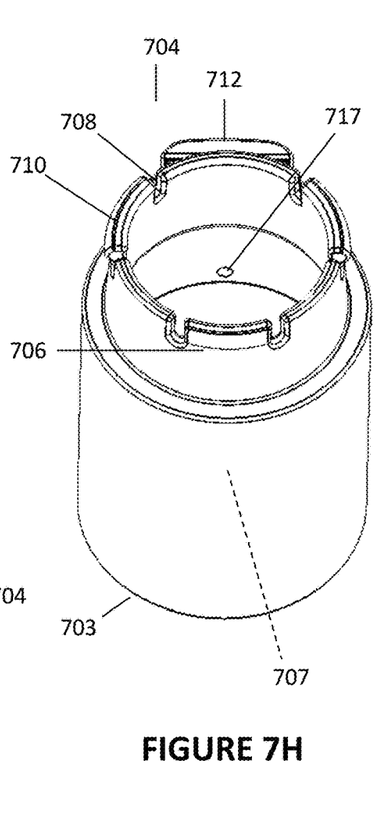
Figure 7I:
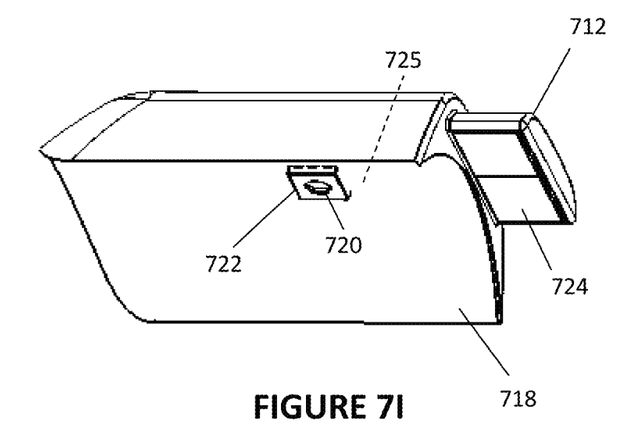

The sensor module 700 can be attached to the outlet 119. FIG. 7B shows a sequence of cross-sections illustrating function of the end portions 706 of the body 702 of the sensor module 700. When the sensor module 700 is urged against the cuff 118, the end portions 706 cantilever inwardly as the wall of the cuff 118 defining the outlet 119 brushes against the curved ridges 710. If the sensor module 700 is urged further against the cuff 118, the curved ridges 710 pop or snap into place in the depressions 124 located on sections of the inner wall of the cuff 118.

The sensing element 718 module 700 comprises an input device 714. In the illustrated configuration the input device 714 comprises a depressible member such as a button. The input device 714 is configured or adapted to transmit an input signal to a controller adapted to control components of the respiratory therapy system 100 (for example, the controller 111 described elsewhere in this disclosure with reference to FIG. 1). In some configurations, the input device 714 may comprise other devices, including but not limited to buttons, knobs, dials, switches, levers, touch screens, or microphones. The controller receiving the input signal may change a number of parameters or functions dependent on the component controlled. For example, the input signal may be used to trigger one or more of the following: turning a flow generator or humidifier on or off, activating a pressure and/or flow ramping function of a respiratory therapy device, increasing and/or decreasing a target humidity level, increasing and/or decreasing a target temperature level, and activating and/or deactivating a patient wakefulness-dependent pressure response algorithm (e.g. an algorithm that modulates pressure of gases delivered by, for example, the flow generator 102 dependent on a sleep state of a patient using the respiratory therapy system 100). In some configurations, actuating the input device in a first manner will send a first signal to the controller 111 and actuating the input device in a second manner will send a second signal to the controller 111. For example, pressing the button for a short period of time may cause the pressure of gases delivered by the flow generator 102 to decrease, and depressing the button for a prolonged period of time may cause the flow generator 102 to be turned off. In some configurations, input signals from the input device 714 may be transmitted to the heating wire 114 by superimposing an input signal over the heating wire 114. The superimposition of the input signals may be similar to the superimposition of the data signal described elsewhere in this disclosure. In other configurations, the input signal may be transmitted to components of the respiratory therapy system 100 wirelessly, e.g. using RFID or wireless communications technologies including but not limited to Wi-Fi, Bluetooth, 2G, 3G, or 4G.

The sensor module 700 additionally comprises an output device 716. In the illustrated configuration the output device 716 comprises a light-emitting display (LED). In other configurations, the output device 716 may comprise, for example, displays, speakers, or vibrating/tactile output elements. In some configurations, the output device 716 communicates with a microcontroller 732 attached to the PCB 725. In some configurations, the microcontroller 732 is configured to receive data signals from one or more of the components of a respiratory therapy system to which the sensor module 700 is attached. Data signals received may be transmitted to the microcontroller 732 (using, for example, the heating wire 114 as described elsewhere in this disclosure, or through RFID or wireless communications technologies including but not limited to Wi-Fi, Bluetooth, 2G, 3G, or 4G). The microcontroller 732 may communicate with the output device 716 to inform the patient or user about operating conditions or parameters of the components of the respiratory therapy system 100. In some configurations, the output device 716 may alert or warn the patient of leaks or fault conditions. For example, the LED of the output device 716 may flash if a significant gas leak is determined at one of the components, or if a fault condition of one of the components is determined. In some configurations, the LED may blink for a predetermined period of time during therapy, e.g. during the first 5 seconds of therapy, to reassure the user that the sensor module 700 is operational.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to."

Where, in the foregoing description reference has been made to integers or components having known equivalents thereof, those integers or components are herein incorporated as if individually set forth.

The disclosed methods, apparatus and systems may also be said broadly to comprise the parts, elements and features referred to or indicated in the disclosure, individually or collectively, in any or all combinations of two or more of said parts, elements or features.

Reference to any prior art in this specification is not, and should not be taken as, an acknowledgement or any form of suggestion that that prior art forms part of the common general knowledge in the field of endeavour in any country in the world.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Moreover, not all of the features, aspects and advantages are necessarily required to practice the present disclosure. Accordingly, the scope of the present disclosure is intended to be defined only by the claims that follow.

What is claimed is:

1. A sensor module comprising:
a housing adapted to be releaseably coupled to a conduit of a respiratory therapy system, the housing comprising:
a gases sampling passageway adapted to receive gases from a lumen of the conduit;
one or more sensors adapted to determine one or more characteristics of gases located within the gases sampling passageway;
a controller adapted to transmit a data signal outputted by the one or more sensors to at least one component of the respiratory therapy system; and
a physical interface adapted to releaseably couple the housing with a complementary conduit physical interface on an exterior of the conduit such that the gases sampling passageway is aligned with a pneumatic outlet of the conduit and the one or more sensors receive the gases through the gases sampling passageway.

2. The sensor module of claim 1, wherein the controller is adapted to wirelessly transmit the data signal to the at least one component of the respiratory therapy system.

3. The sensor module of claim 1, wherein the sensor module further comprises an electrical interface adapted to form an electrical connection with a complementary conduit electrical interface, wherein the physical interface is adapted to align the electrical interface with the conduit electrical interface.

4. The sensor module of claim 3, wherein the electrical interface is adapted to form an electrical connection with a heating wire positioned in, on, around or near the conduit.

5. The sensor module of claim 4, wherein the sensor module is adapted to transmit the data signal from the one or more sensors to the at least one component by superimposing the data signal over a power signal of the heating wire.

6. The sensor module of claim 1, wherein the physical interface comprises a side protrusion adapted to fit through a corresponding aperture on the conduit physical interface.

7. The sensor module of claim 6, wherein the physical interface is a snap fit mechanism.

8. The sensor module of claim 1, wherein the sensor module further comprises a tab adapted to be manipulated to facilitate release of the sensor module from the conduit physical interface.

9. The sensor module of claim 1, wherein the gases sampling passageway extends in a direction substantially perpendicular to the lumen.

10. The sensor module of claim 1, further comprising an aperture allowing for communication between the gases sampling passageway and ambient air outside of the respiratory therapy system.

11. The sensor module of claim 1, wherein one or more of the sensors comprise a membrane that allows for passage of water vapour without allowing for passage of liquid water.

12. The sensor module of claim 1, wherein the sensor module is adapted to be positioned between the conduit and a patient interface.

13. The sensor module of claim 1, wherein the one or more sensors is positioned outside of but in pneumatic communication with the lumen.

14. The sensor module of claim 1, wherein the housing comprises a cover and a base, wherein the cover and the base are coupled together.

\* \* \* \* \*